US005787187A

United States Patent [19]
Bouchard et al.

[11] Patent Number: 5,787,187
[45] Date of Patent: Jul. 28, 1998

[54] SYSTEMS AND METHODS FOR BIOMETRIC IDENTIFICATION USING THE ACOUSTIC PROPERTIES OF THE EAR CANAL

[75] Inventors: Ann Marie Bouchard; Gordon Cecil Osbourn, both of Albuquerque, N. Mex.

[73] Assignee: Sandia Corporation, Albuquerque, N. Mex.

[21] Appl. No.: 626,704

[22] Filed: Apr. 1, 1996

[51] Int. Cl.$^6$ .................... G06K 9/00; G07D 7/00
[52] U.S. Cl. .............. 382/115; 382/118; 340/825.34; 902/3; 235/382
[58] Field of Search ............ 382/115–118; 340/825.3, 340/825.31, 825.34; 902/3, 5; 235/379–382; 364/DIG. 1, DIG. 2; 73/579, 585, 587; 181/0.5, 123, 126–135; 705/18, 44; 395/2.09, 2.4, 2.55, 2.82, 2.83; 381/60, 68, 68.2, 68.3; 367/191, 13; 128/746, 920, 630, 647, 660.01

[56] References Cited

U.S. PATENT DOCUMENTS

| Re. 29,008 | 10/1976 | Ott .................................. | 128/660 |
|---|---|---|---|
| 3,872,443 | 3/1975 | Ott .................................. | 73/579 |
| 4,107,775 | 8/1978 | Ot .................................. | 128/660 |
| 5,105,822 | 4/1992 | Stevens et al. ....................... | 128/746 |
| 5,335,288 | 8/1994 | Faulkner ............................ | 382/4 |
| 5,414,755 | 5/1995 | Bahler et al. ....................... | 379/67 |
| 5,432,864 | 7/1995 | Lu et al. ........................... | 382/118 |
| 5,456,256 | 10/1995 | Schneider et al. ................... | 128/660.09 |
| 5,465,290 | 11/1995 | Hampton et al. .................... | 379/67 |
| 5,483,601 | 1/1996 | Faulkner ............................ | 382/115 |
| 5,659,625 | 8/1997 | Marquardt .......................... | 382/118 |

FOREIGN PATENT DOCUMENTS 2678821  1/1993  France .

OTHER PUBLICATIONS

Ali, "Plastic with a Brain", CMA Magazine, pp. 11–13, May, 1994.
Herbert Gish and Michael Schmidt, *Text–Independent Speaker Identification*, IEEE Signal Processing Magazine, vol. 11, No. 4, pp. 18–32 (Oct. 1994).
Lawrence Rabiner and Biing–Hwang Juang, *Fundamentals of Speech Recognition*, pp. 112–117, Prentice Hall, Inc., Englewood Cliffs, New Jersey (1993).
Sally A. Gaskill and Ann M. Brown, *The Behavior of the Acoustic Distortion Product, 2f1–2f2, from the Human Ear and its Relation to Auditory Sensitivity*, J. Acoust. Soc. Am., vol. 88, No. 2, pp. 821–839 (Aug. 1990).
Michael R. Stinson and B. W. Lawton, *Specification of the Geometry of the Human Ear Canal for the Prediction of Sound–Pressure Level Distribution*, J. Acoust. Soc. Am., vol. 85, No. 6, pp. 2492–2503 (Jun. 1989).
Herbert Hudde, *Measurement of the Eardrum Impedance of Human Ears*, J. Acoust. Soc. Am., vol. 73, No. 1, pp. 242–247 (Jan. 1983).

(List continued on next page.)

*Primary Examiner*—Leo Boudreau
*Assistant Examiner*—Bhavesh Mehta

[57] ABSTRACT

The present invention teaches systems and methods for verifying or recognizing a person's identity based on measurements of the acoustic response of the individual's ear canal. The system comprises an acoustic emission device, which emits an acoustic source signal s(t), designated by a computer, into the ear canal of an individual, and an acoustic response detection device, which detects the acoustic response signal f(t). A computer digitizes the response (detected) signal f(t) and stores the data. Computer-implemented algorithms analyze the response signal f(t) to produce ear-canal feature data. The ear-canal feature data obtained during enrollment is stored on the computer, or some other recording medium, to compare the enrollment data with ear-canal feature data produced in a subsequent access attempt, to determine if the individual has previously been enrolled. The system can also be adapted for remote access applications.

57 Claims, 4 Drawing Sheets

OTHER PUBLICATIONS

Sadaoki Furui, *Cepstral Analysis Technique for Automatic Speaker Verification*, IEEE Trans. On Acoustics, Speech, and Signal Processing, vol. ASSP-29, pp. 254–272 (Apr. 1981).

P. A. Johansen, *Measurement of the Human Ear Canal*, Acustica, vol. 33, pp. 349–351 (1975).

B. S. Atal, *Effectiveness of Linear Prediction Characteristics of the Speech Wave for Automatic Speaker Identification and Verification*, J. Acoust. Soc. Am., vol. 55, No. 6, pp. 1304–1312 (Jun. 1974).

B. S. Atal and Suzanne L. Hanauer, *Speech Analysis and Synthesis by Linear Prediction of the Speech Wave*, J. Acoust. Soc. Am., vol. 50, No. 2, pp. 637–655 (1971).

A. Michael Noll, *Cepstrum Pitch Determination*, J. Acoust. Soc. Am., vol. 41, No. 2, pp. 293–309 (1967).

Synthesis and Characterization of $Bi_4Ti_3O12$ Thin Films by Sol Gel Processing; Masashiro Toyoda, Yukio Hamaji, Kunisaburo Tomono and Daivd A. Payne, Jpn. J. Appl. Phys., vol. 32 (1993) Part No. 9B.

SYSTEMS AND METHODS FOR BIOMETRIC IDENTIFICATION USING THE ACOUSTIC PROPERTIES OF THE EAR CANAL

GOVERNMENT RIGHTS

This invention was made with United States Government support under Contract No. DE-AC04-94AL85000 awarded by the U.S. Department of Energy. The Government has certain rights in this invention.

BACKGROUND OF THE INVENTION

The present invention relates generally to the field of identity verification or recognition (e.g., to ascertain authorization to access a secure facility, controlled information, a bank or computer account, etc.). More specifically, the present invention relates to systems and methods for identity verification/recognition by using the acoustic properties of the ear canal as a biometric—a set of measurements of physical traits of the individual attempting access. Generally, the term "biometric" refers to use of measurements of a person's physical characteristics as a basis for recognition of the person, typically by a machine. A biometric can also include behavioral characteristics, such as the manner in which a person writes his/her signature.

Identity verification/recognition can be achieved in essentially three ways: (1) by possession of knowledge, such as a password or personal identification number ("PIN"); (2) by possession of an object/escort memory device, for example, identification card, a badge, an encoded magnetic card, badge, or key; or (3) by possession of a biometric, a set of measurable physical traits of the individual's person, such as a fingerprint, hand, voiceprint, face, vein patterns, or iris or retinal scan. Passwords or PINs can be forgotten or compromised, and escort memory devices are vulnerable to loss, theft, or forgery. Additionally, to avoid remembering (or forgetting) a different password or PIN for each of an increasing number of different accounts, people will often write down the passwords, or assign the same passwords to many accounts, making not one, but several, of the information resources more vulnerable to compromise. Biometrics have a distinct advantage over passwords and escort memory devices, in that biometrics cannot be forgotten or lost and are difficult for an impostor to reproduce. However, no currently commercially-available biometric technology has gained wide use, because none is both highly reliable and acceptable to users.

Unacceptable error rates (poor reliability) result from too much similarity among individuals, too much variability for each individual, or both. At enrollment of an authorized individual, a set of biometric features, or "pattern," is measured a number of times and stored in a database. It is hoped that this set of patterns is a good representation of the individual's day-to-day variability. When an individual seeks access, that individual's pattern is measured anew and compared with those stored, for example, in the database. If the individual's new pattern matches one's own patterns that were previously stored in the database, then access is granted. However, if the patterns of different individuals (including impostors not in the database) are too similar, then an impostor can be allowed access as an authorized user, which is termed a "false accept" error. Conversely, if an authorized individual's pattern changes too much from day to day, then the new pattern fails to match those stored in the database closely enough, and such a person can be denied access, which is termed a "false reject" error. In high-consequence situations, either false accept or false reject errors can be catastrophic. These errors indicate that either the choice of measurements is not unique to an individual or that not enough representations are stored in the database. Hence, an optimized choice of features and data are crucial to success.

In general, a key, desirable quality of a successful biometric system for identity verification/recognition is user acceptance. Other key requirements for successful biometric identity verification/recognition are reliability, fast verification, low cost, durability, and quick and convenient enrollment. Some factors impacting the success of a biometric technology at meeting these requirements are the uniqueness and variability of the features selected to identify a person, the nature and amount of interaction required of the person, and the sensor sensitivity and computing power required for feature extraction and pattern recognition. Pattern recognition uses an existing set of training data that have identified groupings or classes and assigns a class identity grouping to newly-measured test data.

Not only must a biometric technology be reliable, but users must deem it acceptable. Many users feel uncomfortable with placing their eyes very close to a sensing device, as is required in retinal scans. Even though a retinal scan is a very reliable biometric, it is unlikely to be used for many applications because of the low level of user acceptance. Other biometrics can be rejected by users because of privacy issues or the perception that the sensing system is unsafe. In addition, if the enrollment process is tedious or time consuming, or if the time lag between beginning an access attempt and receiving the verification/recognition response is too long (more than a few seconds), users can find the process unacceptable. The successful biometric technology must have appropriate sensors and computing power to extract features and perform pattern recognition very rapidly. In addition, the sensing device must be perceived by users to be non-threatening, non-invasive, and comfortable.

The prior art is replete with identity verification/recognition systems that employ the use of a biometric. Examples of some of the prior art patents are the following:

U.S. Pat. Nos. 5,483,601 [Faulkner, *Apparatus and Method for Biometric Identification Using Silhouette and Displacement Images of a Portion of a Person's Hand*, U.S. Pat. No. 5,483,601] and 5,335,288 [Faulkner, *Apparatus and Method for Biometric Identification*, U.S. Pat. No. 5,335,288.], wherein Faulkner teaches a biometric apparatus for recognizing a user's identity based on measurements performed on the user's hand. The apparatus stores hand feature data obtained during an enrollment operation cycle to compare with hand feature data obtained during a subsequent hand bid operation cycle to determine if the user had been previously enrolled on the biometric apparatus. Faulkner teaches the use of measurements performed on a person's hand, namely, the use of a silhouette image of a person's hand and displacement images.

U.S. Pat. No. 5,465,290 [Hampton et al., *Confirming Identity of Telephone Caller*, U.S. Pat. No. 5,465,290.], wherein Hampton et al. teach a distributed information processing system for verifying the identities of telephone callers. Additionally, Hampton et al. discuss voice processors or speaker verification units for processing the voiceprint of a person for remote access applications.

U.S. Pat. No. 5,546,256 [Schneider et al., *High Resolution Ultrasonic Imaging Apparatus and Method*, U.S. Pat. No. 5,546,256.], wherein Schneider et al. teach an ultrasonic imaging system and method for imaging the surface of human or animal tissue. The invention of Schneider et al. can be applied in the area of fingerprint scanning and imaging.

U.S. Pat. No. 5,432,864 [Lu et al., *Identification Card Verification System*, U.S. Pat. No. 5,432,864.], wherein Lu et al. teach an apparatus and method for verifying the identity of a person by comparing that person's face (or selected facial features) with an image generated using data stored on an identification escort memory carried by that person. Lu et al. generate a master set of facial appearances or features by selecting a number of people that have a wide range of facial appearances, or alternatively, who have a wide range of facial features, such as ear shapes. Lu et al., however, do not teach the use of the ear canal shape, as opposed to the ear shape, as a biometric.

U.S. Pat. No. 5,414,755 [Bahler et al., *System and Method for Passive Voice Verification in a Telephone Network*, U.S. Pat. No. 5,414,755.], wherein Bahler et al. teach a long distance telephone service using speaker verification to determine whether a user is a valid user. The identity of the user is verified by comparing, either during or after the call, the signals in accordance with an algorithm which compares a reference utterance of a known customer with input utterances from one or more unknown telephone service users, one of which users has claimed the identity of the customer.

The present invention differs from the above-cited patents because it provides for the measurement of a different biometric, or physical characteristic, which is the ear canal. Unlike the inventions of Lu et al. (U.S. Pat. No. 5,432,864), Schneider et al. (U.S. Pat. No. 5,546,256), and Faulkner (U.S. Pat. Nos. 5,483,601 and 5,335,288), the present invention uses acoustic data as opposed to image data.

SUMMARY OF THE INVENTION

The present invention comprises a system for recognizing or verifying a person's identity based on measurements performed on the person's ear canal with the system generally comprising the combination of data acquisition means for storing biometric information from an ear canal of an individual; source means for transmitting source signals into an ear canal of the individual; recording means for recording response signals emitted from the ear canal of the individual; and means for verifying or recognizing that the response signals match the biometric information from the ear canal of the individual to determine whether the individual was previously enrolled.

The present invention also comprises a method of verifying or recognizing a person's identity based on measurements performed on the person's ear canal with the method generally comprising the combination of the steps: enrolling an individual to obtain a reference or baseline; transmitting source signals into an ear canal of an individual; detecting response signals emitted from the ear canal of the individual; and comparing the reference signals against the response signals emitted from the ear canal of the individual to determine whether the individual was previously enrolled.

The scope of applicability of the present invention can be realized and attained by means of the instrumentalities and combinations particularly pointed out in the appended claims. Further scope of applicability of the present invention will become apparent from the detailed description of the invention provided hereinafter. Similarly, certain objects, advantages, and novel features will become apparent to those of ordinary skill in the art upon examination of the following detailed description of the invention or may be learned by practice of the present invention. It should be understood, however, that the detailed description of the invention and any specific examples presented, while indicating certain embodiments of the present invention, are provided for illustration purposes only because various changes and modifications within the spirit and scope of the invention will become apparent to those of ordinary skill in the art from the detailed description of the invention and claims that follow.

BRIEF DESCRIPTION OF THE DRAWINGS

The accompanying figures, which are incorporated in and form part of the specification, further illustrate the present invention and, together with the detailed description of the invention, serve to explain the principles of the present invention.

DETAILED DESCRIPTION OF THE INVENTION

The present invention comprises a novel biometric system designed for reliability and user acceptance. The present invention uses the acoustic properties of the ear canal as a biometric. The present invention takes advantage of the following: (1) individual ear canal shapes are unique; (2) acoustic signals associated with the ear canal, such as impedance or acoustic distortion product, are unique to the individual; (3) acoustic signals associated with the ear canal are reproducible over a time scale from weeks to years; and (4) the response signal reflected from the ear canal is sufficiently strong to be measurable.

No previous work in the field discloses, teaches, or suggests the use of the acoustic properties of the ear canal as a biometric. P. A. Johansen, Michael R. Stinson and B. W. Lawton have shown that individual ear canal shapes are unique to the individual. [P.A. Johansen, *Measurement of the Human Ear Canal*, Acustica, 33, 349–351 (1975); Michael. R. Stinson and B. W. Lawton, *Specification of the Geometry of the Human Ear Canal for the Prediction of Sound-Pressure Level Distribution*, J. Acoust. Soc. Am., 85 (6), pp. 2492–2503 (June 1989).]. Furthermore, Stinson and Lawton have demonstrated that the acoustic resonances and attenuations associated with the ear canal shape are unique. [Michael. R. Stinson and B. W. Lawton, *Specification of the Geometry of the Human Ear Canal for the Prediction of Sound-Pressure Level Distribution*, J. Acoust. Soc. Am., 85 (6), pp. 2492–2503 (June 1989).] For example, FIG. 9 of the Stinson and Lawton article illustrates a comparisons of fifteen ear canal molds studied. FIG. 10, p. 2499, of the Stinson and Lawton article illustrates the cross-sectional area of each of the fifteen ear canals studied, as a function of position along a curved center axis. Again, area function is shown to be unique to the individual. Thus, if the frequencies or intensities associated with these resonance and attenuation features are used to verify/recognize an individual's identity, then it is expected that the inter-individual similarity and intra-individual variability, which results in unreliable verification/recognition, should be minimal.

Quantitative measurements that are characteristic of the shape of the ear canal will also be unique. Stinson and Lawton have calculated the transformation of the sound press level ("SPL") using the ear canal shape as input to the calculation. Although FIG. 14 of the Stinson and Lawton article shows this qualitatively, the present invention recognizes that this quantity, SPL, is also very sensitive to ear canal shape, which is unique.

Figure 2:
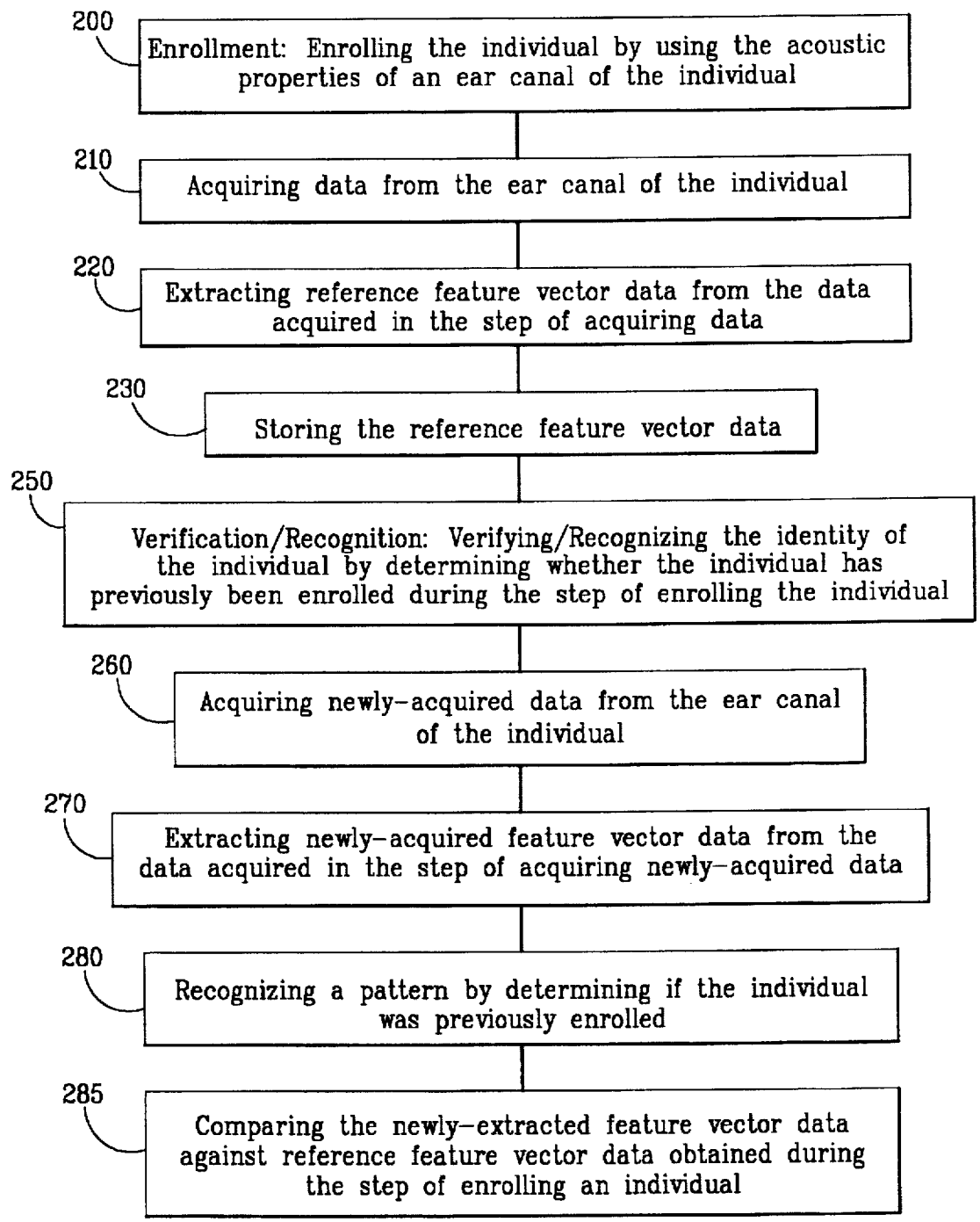
FIG. 2 is a flowchart depicting the method steps in accordance with the present invention.

In addition, Sally A. Gaskill and Ann M. Brown have shown that an individual's acoustic signal can remain stable and consistent over long time scales, such as for several months. [Sally A. Gaskill and Ann M. Brown, *The Behavior of the Acoustic Distortion Product, 2f1–2f2, from the Human Ear and its Relation to Auditory Sensitivity*, J. Acoust. Soc. Am., 88 (2), pp. 821–839 (August 1990).] FIG. 3 of the Gaskill and Brown article demonstrates that the acoustic distortion product is reproducible in an individual, on time scales over a year long for at least one subject. FIG. 2 of the Gaskill and Brown article demonstrates that the acoustic distortion product from the ear differs from individual to individual. In fact, the manner in which the acoustic distortion product varies with similar level varies from individual to individual.

Herbert Hudde demonstrates that eardrum impedance is unique in six individuals that were investigated (see Hudde, FIG. 4, p.245) and that the impedance measurements are highly reproducible. [Herbert Hudde, *Measurement of the Eardrum Impedance of Human Ears*, J. Acoust. Soc. Am. 73 (1), pp. 242–247 (January 1983).] FIG. 7 of the Hudde article demonstrates the high reproducibility of the impedance measurements expressed in reflectance; the two measurements illustrated in FIG. 7 of the Hudde article were obtained in the same ear, three weeks apart.

The measurements described in the articles cited above were obtained under closely-controlled conditions, which were uncomfortable to the human subjects in some cases. The present invention embodies the sensors in, for example, a modified telephone handset or a hand-held apparatus reminiscent of a telephone handset. Because most people use the telephone many times per day, the present invention is expected to be more comfortable to users than those biometric devices that require users to perform a specific action that they do not normally perform many times per day (e.g., place the user's eye near a detector, place the user's hand in a particular position among some placement pegs, etc.). Unlike some more fragile biometric systems, the present invention is expected to be able to sustain the type of abuse typical of public telephone use. In addition, because only acoustic (audible or ultrasound) signal processing is required, the present invention can be less expensive than image-based (e.g., hand geometry images, or pressure sensed images of hand geometry, face images, face profiles, etc.) or video-based biometrics.

Figure 1:
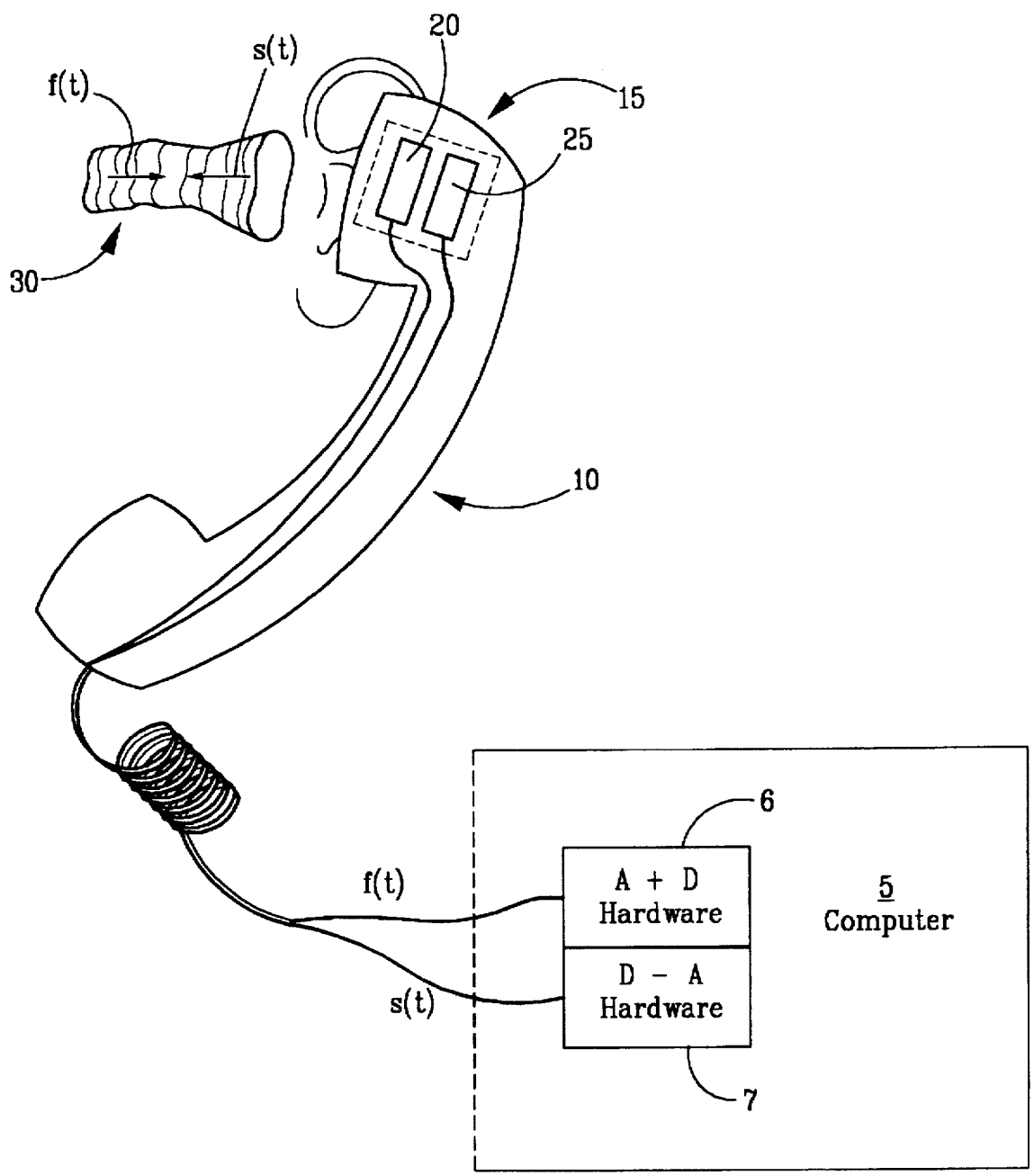
FIG. 1 is a block diagram depicting a biometric identity verification/recognition system in accordance with the present invention.

The various components or subassemblies of the system illustrated in FIG. 1 now will be described in detail. FIG. 1 illustrates a block diagram of one embodiment of the system of the present invention. The hand-held apparatus 10, which the individual seeking access places against the individual's ear, preferably includes both an acoustic source signal emitter 20 and a signal response detector 25. In practice, acoustic source signal emitter 20 is a speaker and signal response detector 25 is a microphone. Source signal emitter 20 and signal response detector 25 can be combined into a transceiver. Depending upon the application, the earpiece of the telephone handset can be closely coupled or molded to the user's ear to minimize background noise. An acoustic source signal s(t) specified by a commercially-available computer 5 through commercially-available digital-to-analog hardware (D-A hardware 7) as a function of time t, is emitted by the acoustic source signal emitter 20 into the individual's ear canal 30 (left-pointing arrow), or other medium or cavity that generates a response signal f(t), e.g., bone material or cartilage. The response signal f(t) can be reflected off of any object near the ear canal itself, such as the pinna—the cartilaginous, projecting flap of the external ear of vertebrates—or the skull, and the present invention is intended to cover emitting signals around or into the ear area and detecting the response signal, whether it was reflected from the ear canal 30 or otherwise. A response signal f(t) (right-pointing arrow) is emitted from the ear canal 30 in response to the acoustic source signal s(t) emitted in the ear canal 30, which is very sensitive to the shape of the ear canal 30, is detected by the signal response detector 25. The response signal f(t) is digitized and sampled at a relatively high sampling rate (e.g., ~200 kHz, the range of 100 Hz to 50kHz, etc.) using commercially-available analog-to-digital (A-D hardware 6) and digital-to-analog hardware in a manner well known to those of ordinary skill in the art. The digitized response signal f(t) is analyzed via a computer-implemented method by computer 5 to extract a feature vector (a set of specific measurements, or features) in accordance with the several embodiments set forth below (e.g., Equations (1)–(6)), which is characteristic of the individual's unique ear canal shape.

In practice, for example, the A-D/D-A hardware 6 and 7 was obtained from supplier Cyber Research with part number HS DAS 16. The A-D/D-A hardware 6 and 7 is a 200 kHz 16-bit analog-to-digital and digital-to-analog DAS board. High-level driver software routines, supplied with the A-D/D-A hardware 6 and 7, are used to send the source signal s(t) and receive the response signal f(t).

The digitized response signal can be encrypted to enhance security or compressed to enhance computation speed, thus, minimizing (transmission) costs. Encryption, of course, conceals a message from all those who do not have the proper decryption key and validates a message as having been sent by a person having the proper encryption key.

At enrollment, the individual places the hand-held apparatus 10 to the individual's ear and this process, i.e., emission, detection, and feature extraction, is completed such that several feature vectors are extracted for the individual, and stored in a storage medium (not shown explicitly because it is included in computer 5), e.g., in a database, on a magnetic strip card, on an optical storage card, on a smart card (Smart cards are plastic cards similar in size to a standard credit card.), on a semiconductor storage card such as static random access memory ("SRAM"), programmable read only memory ("PROM"), erasable PROM ("EPRO"), etc. One option is to simply encode the biometric data into the memory of the storage medium. When the individual attempts access, the individual places the hand-held apparatus 10 to the individual's ear and a source signal s(t) is emitted into an ear canal 30 of the individual. The emission, detection, and feature extraction process is completed. The data associated with the claimed identity is then read out of the storage medium (not shown)

and computer 5 is used to compare the newly-acquired feature vector against the previously stored features via a pattern recognition method. One such pattern recognition method that can be used in the present invention is presented by Gordon C. Osbourn and Rubel F. Martinez in *Visual Cluster Analysis and Pattern Recognition Template and Methods*, U. S. Pat. application Ser. No. 08/174,548, filed on Dec. 28, 1993. Such pattern recognition methods are well within the abilities of those skilled in pattern recognition and clustering analysis and need not be discussed further for an understanding of the present invention. If a close match is found, then the individual is granted access. If a close match is not found, then the individual is denied access or additional access attempts can be allowed depending on the application or configuration.

The various steps comprising the method as outlined in FIG. 2 now will be described in detail. The method of the present invention for identity verification/recognition of an individual comprises, in a broad sense, the steps of enrolling and verifying/recognizing the identity of an individual. Verification differs from recognition as follows: verification compares reference information pertaining to an individual against later-obtained information pertaining to the same individual, whereas recognition compares reference information pertaining to a group of individuals against information pertaining to an individual.

Enrollment, Step 200, the step of enrolling an individual in accordance with the present invention, comprises the steps of Step 210 acquiring data, Step 220 extracting features, and Step 230 storing the feature data on a some storage medium, such as a computer, magnetic stripe, etc. The steps of acquiring data and extracting features for the present invention are described below.

Verification, Step 250, the step of verifying the identity of the individual (e.g., upon access attempt) in accordance with the present invention, comprises the steps of Step 260 acquiring data, Step 270 extracting features, and Step 280 recognizing a pattern. Enrollment precedes verification. Data acquisition and feature extraction for the present invention are described below. The step of recognizing a pattern, i.e., pattern recognition, comprises the step of Step 285 comparing newly-extracted feature vector data from the newly-acquired data against the feature vector data stored at enrollment for the individual whose identity is claimed using a computer-implemented pattern recognition algorithm. If a sufficiently close match is found (depending on the particular pattern recognition algorithm employed), then the individual's identity is verified, and access is granted. If the match is insufficiently close, then the individual's identity is not verified, and access is denied or further access attempts are allowed depending on the requirements. For identity verification, a means for accessing the previously stored feature data of the claimed identity is required. For example, the individual attempting access can be required to supply a PIN that can be used to locate previously stored feature data on a computer; or the individual can be required to supply, for example, a magnetic strip card containing the previously stored feature data. The particular choice of such a means is not essential to the present invention and, therefore, will not be discussed; the means will be selected according to the application in a manner that will become apparent to those of ordinary skill in the art.

Recognition, the step of Step 250 recognizing an individual in accordance with the present invention, comprises the steps of Step 260 acquiring data, Step 270 extracting features, and Step 280 recognizing a pattern. Enrollment precedes recognition. Data acquisition and feature extraction for the present invention are described below. The step of recognizing a pattern, i.e., pattern recognition, comprises the step of Step 285 comparing newly-extracted features from the newly-acquired data against the feature vector data stored at enrollment for all of the individuals in the database using a computer-implemented pattern recognition algorithm. If a sufficiently close match is found with the stored features of at least one individual, then the identity of the best matched individual is recognized, and access is granted. If the match is insufficiently close to any individual's feature data in the database, the individual is not recognized, and access is denied.

The steps 210 and Step 260 of acquiring data comprises the steps of emitting an acoustic source signal s(t) into the ear canal as a function of time t and detecting the response signal f(t) reflected by the ear canal 30. The acoustic source signals s(t) can be emitted as a function of time into the ear canal through an acoustic source signal emitter 20, and the response signal f(t) reflected by the ear canal 30 can be detected with a signal response detector 25 as shown in FIG. 1. The source signal s(t) is typically a known/controlled acoustic source signal s(t) having a well-characterized frequency content from zero Hz up to a maximum frequency, which can vary from one embodiment to another. The source signal s(t) can be provided for example, by a computer 5—the biometric system administrator—through digital-to-analog hardware that can be connected to the signal response detector 25. The response signal f(t) is digitized and sampled at a high sampling rate (e.g., 200 kHz), using conventional analog-to-digital hardware, and the digitized signal data is recorded, for example, on the computer 5.

Features are then extracted from the digitized signal data using computer-implemented algorithms. An important aspect of the invention is the feature vector used to characterize the individual. Many features are possible; several different sets of feature vectors are discussed below. The goal is to capture the frequency and intensity information from the response signal f(t reflected from the ear canal 30 which is most unique and reproducible to the individual in some relatively small set of features, for example, in the range of 10 to 50 features. A number of different embodiments with different sets of feature vectors are described below.

Figure 3:
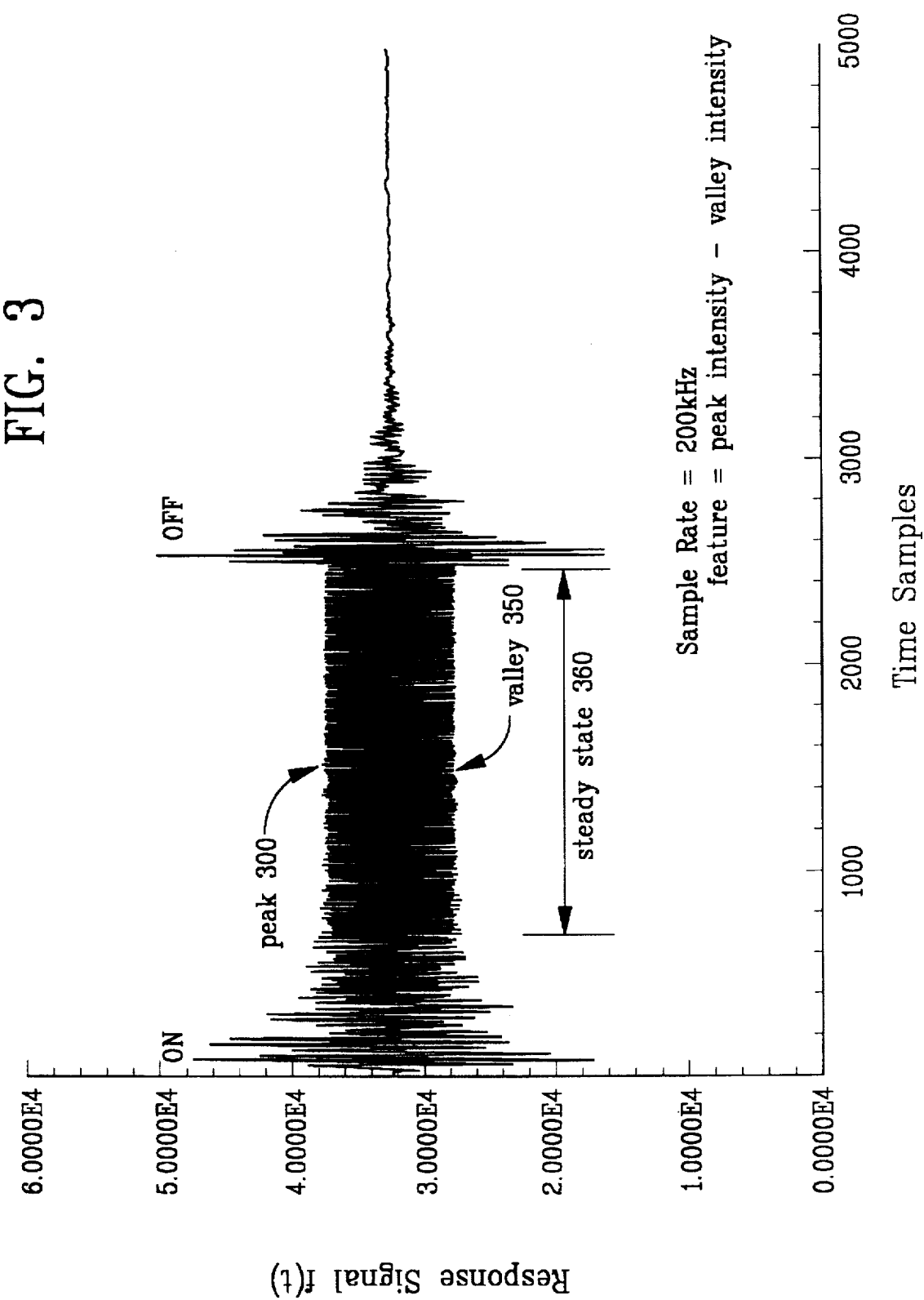
FIG. 3 is an example of a feature extracted from the response signal f(t) in accordance with the present invention—the peak-to-valley difference of the response (steady-state) signal f(t) for a single frequency in the series.

In one embodiment of the present invention, the source signal s(t) is a series of pure-frequency tones of sufficient duration (e.g., on the order of 100 complete cycles) that a steady state is reached in the response signal f(t) for each frequency. The source signal s(t) can be, for example, a series of frequency tones from 1 kHz to 20 kHz in increments of 100 Hz. A collection of feature vectors can be extracted from the response signal f(t), including the peak-to-valley difference of the detected steady-state signal for each frequency in the series. FIG. 3 illustrates an example of a feature extracted from the response signal f(t) in accordance with the present invention—the peak-to-valley intensity. FIG. 3, a graph of response signal f(t) versus time samples, illustrates the response difference from peak 300 to valley 350 of the response (steady-state) signal f(t) for a single frequency in the series. Also denoted on FIG. 3 are the ON and OFF states of the system and also the steady state 360 response of the system. This collection of features is similar to a frequency spectrum. The approximate spectrum can be used in whole or in part as a feature vector for the individual, analogous to using the optical spectrum to identify materials.

In another embodiment of the present invention, the source signal s(t) comprises broad-band noise. The spectrum, or discrete Fast Fourier Transform, $F(\omega)$, of the response signal f(t) is computed, and this discrete collection of values, $F(\omega)$, can be used in whole or in part as a feature vector for the individual. This is analogous to using the optical spectrum to identify materials.

In yet another embodiment of the present invention, a known/controlled source signal s(t) is used explicitly to compute the feature vector. The response signal f(t) can be described as a convolution of the source signal s(t) with an effective impulse response function of the ear canal h(t) as follows:

$$f(t)=s(t)*h(t).\qquad\text{Eq. (1)}$$

"h(t)" is referred to as the effective impulse response function of the ear canal because the (detected) response signal f(t) may be a linear combination of the source signal s(t) itself and the filtered, reflected output signal h(t) of the ear canal.

The Fast Fourier Transform ("FFT") of Eq. (1) is:

$$F(\omega)=S(\omega)\,H(\omega),\qquad\text{Eq. (2)}$$

where $F(\omega)$, $S(\omega)$, and $H(\omega)$ are the FFTs of f(t), s(t), and h(t), respectively. Determining the absolute square of the FFT $F(\omega)$ results in the power spectrum $|F(\omega)|^2$. By determining the logarithm of the power spectrum $|F(\omega)|^2$, the effects of the source $S(\omega)$ and the effective impulse response function $H(\omega)$ of the ear canal are effectively separated as follows:

$$\log |F(\omega)|^2 = \log [|S(\omega)|^2|H(\omega)|^2] = \log |S(\omega)|^2 + \log |H(\omega)|^2 \qquad\text{Eq. (3)}$$

Because source signal s(t) is known/controlled, $\log |S(\omega)|^2$ in the above Eq. (3) can be determined in a manner well known to those of ordinary skill in the art. Because response signal f(t) is measured, $\log |F[(\omega)]|^2$ in the above Eq. (3) can also be determined in a manner well known to those of ordinary skill in the art. Therefore, the (discretized) function, $\log |H(\omega)|^2$, can be determined directly for any specified or known source signal s(t) and measured response signal f(t) as follows:

$$\log |H(\omega)|^2 = \log |F(\omega)|^2 - \log |S(\omega)|^2.\qquad\text{Eq.(4)}$$

The present invention takes advantage of the ear canal biometric's active sensor system to directly remove the source signal s(t) (as shown in Eq. (4)). Thus, at least three embodiments of the present invention would use as a feature vector: (1) the discretized $\log |H(\omega)|^2$ as a function of the natural frequency $\omega$, in whole or in part; (2) the discretized $H(\omega)$ as a function of the natural frequency $\omega$, in whole or in part; or (3) the discretized h(t) as a function of time, in whole or in part, all of which can be determined in a manner well known to those of ordinary skill in the art. It is intended that the present invention be adapted to verify/recognize an individual based on the acoustic properties of the ear canal, including complex signals, phase, magnitude, rectified signals, exponentiated signals, instantaneous power, etc.

A novel aspect and important advantage of the present invention in the three embodiments presented above is that, if the source signal (i.e., source function) s(t) is used to determine the feature vector, then the source signal s(t) can be different at each access attempt. In that case, a different response signal (i.e., response function)f(t) is measured at each access attempt, but the same feature vector is obtained. Hence, if an impostor attempts to defeat the system by responding to a new source signal $s_2(t)$ by reproducing the response signal $f_1(t)$ recorded during a previous successful access attempt in which a different source signal $s_1(t)$ was used, then it will not result in a computed feature vector that matches the previously stored version. The ability to require a different response signal f(t) at each access attempt reduces the vulnerability to defeat as compared to a system that provides the same measurement at every access attempt. All other biometric technologies rely on the same data being obtained at each access attempt.

In still another alternative embodiment of the present invention, an alternative feature vector can be used. The "cepstrum function $c(\tau)$" is defined as the power spectrum of the log power spectrum, or alternatively, the square of the inverse FFT of the log power spectrum:

$$c(\tau)=|F^{-1}(\log |F(\omega)|^2)|^2,\qquad\text{Eq.(5)}$$

where $F^{-1}$ denotes the inverse FFT. Eq. (5) is the inverse FFT of Eq. (3), which is the log power spectrum. In the case of the voice (see, for example, A. Michael Noll, *Cepstrum Pitch Determination*, J. Acoust. Soc. Am., 41, pp. 293–309 (1966)), the effect of the source (vocal folds or vocal cords) and the effect of the vocal tract are well separated in $\tau$. If, in the present invention, the source signal s(t) is designated by the computer 5 to resemble the effect of the vocal folds, i.e., a quasi-periodic source resulting in a "high-frequency" ripple in the logarithm power spectrum, then it is reasonable to expect that the effects of the source and the ear canal 30 are well separated in $\tau$. Thus, the cross-term in the square of the rms ("root-mean-square") can be neglected to obtain:

$$c(\tau)=|F^{-1}(\log |H(\omega)|^2)|^2+|F^{-1}(\log |S(\omega)|^2)|^2.\qquad\text{Eq.(6)}$$

Analogous with voice recognition (as discussed in Noll's article), the high-$\omega$ portion of the cepstrum function is associated with the pitch period of the source, and the low-$\omega$ portion is associated with the ear canal 30. (See also p.296, FIGS. 3 and 4 of Noll's article. Note that in FIG. 4 of Noll's article, dq should be d$\omega$.) The feature vector of the present invention comprises the (discretized) low-$\tau$ (ear canal) portion of the function $c(\tau)$. The feature vectors used to identify an individual are the first several (~14 to 20) cepstral values.

It should be noted that if the source signal s(t) is not known accurately, for example, because of degradation of the acoustic source signal emitter 20 or the signal response detector 25 characteristics, then the cepstrum c(t) feature vector can still be used, because the low-$\tau$ portion of the cepstrum contains no information about the source. Alternatively, the high-$\tau$ portion of the cepstrum, which contains only information about the source, can be utilized to monitor the state-of-health of the hand-held apparatus 10 (speaker-microphone system). From the intended source signal s(t), the source-cepstrum (ie., high-$\tau$ portion) can be determined and then compared to the source-cepstrum actually measured. If they are in close agreement, then one of ordinary skill in the art can assume a good state-of-health of the hand-held apparatus 10 (e.g., speaker-microphone system). If the measured source-cepstrum departs significantly from that predicted from the source signal s(t), then one of ordinary skill in the art must assume that the hand-held apparatus 10 is not emitting source signals s(t) or receiving the response signals f(t) accurately, and maintenance or recalibration is warranted.

Thus, the present invention can be easily adapted to have a means of calibration while the earpiece is not in use. For example, if the apparatus hangs so that the earpiece rests directly on a reflective surface, then calibrating signals can be emitted and the response characteristics can be determined when source signals s(t) are simply reflected off of the known reflective surface.

In a further alternative embodiment, the present invention models the ear canal 30 as a discrete time-varying (or constant) linear filter. It is then possible to define a transfer function in the complex Z domain, which can be represented by its poles (the all pole-model). (For more detail, see B. S. Atal and Suzanne L. Hanauer, *Speech Analysis and Synthesis by Linear Prediction of the Speech Wave*, J. Acoust. Soc. Am. 50 (2), pp. 637–655 (1971). The upshot of this embodiment is that one of ordinary skill in the art can predict the current sample from previous samples, and the precise linear combination of the previous samples is obtained by minimizing an error function. The coefficients (called linear predictive coding ("LPC") coefficients) can then be cast into cepstrum coefficients if one assumes the all-pole model. The entire procedure for obtaining LPC coefficients, cepstrum coefficients, and a few other related coefficients can be found in Lawrence Rabiner and Biing-Hwang Juang, *Fundamentals of Speech Recognition*, Prentice Hall, Inc., Englewood Cliffs, N.J. (1993) (specifically, pp. 112–117).

The LPC cepstrum coefficients can be as effective, or even better than, the Fast Fourier Transform ("FT") cepstrum coefficients discussed earlier. According to Sadaoki Furui, *Cepstral Analysis Technique for Automatic Speaker Verification*, IEEE Trans. on Acoustics, Speech, and Signal Processing, Vol. ASSP-29, pp. 254–272 (Apr. 1981), the LPC Cepstrum coefficients were most effective features from LPC analysis for speaker recognition. The FFT cepstrum results were compared to the LPC cepstrum results, but the LPC cepstrum coefficients took about half the computing time.

Figure 1A:
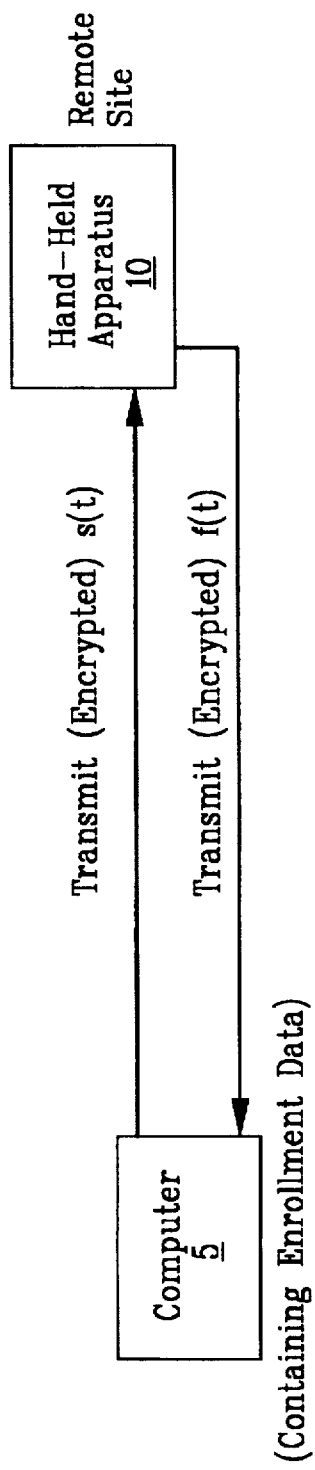
FIG. 1A is a block diagram depicting an embodiment of a biometric identity verification/recognition system for remote access application in accordance with the present invention.

In yet another alternative embodiment, the present invention can be configured to accommodate remote access applications, which is desirable in some cases. Referring to FIG. 1A, a commercially-available computer 5, at a first location, transmits (possibly encrypted) source signals s(t) over a transmission line to a hand-held apparatus at a second location. Computer 5 contains enrollment/reference data pertaining to an individual that has been previously enrolled in the system, and is configured as discussed earlier with reference to FIG. 1 with D-A/A-D hardware. Hand-held apparatus 10 (as discussed earlier with reference to FIG. 1) transmits over a transmission line (possibly encrypted) response signals f(t). Computer S then extracts features from the response signal f(t) and performs pattern recognition using a computer-implemented method as discussed earlier. If the identity of the individual is recognized or verified, then access is granted and vice versa.

Figure 1B:
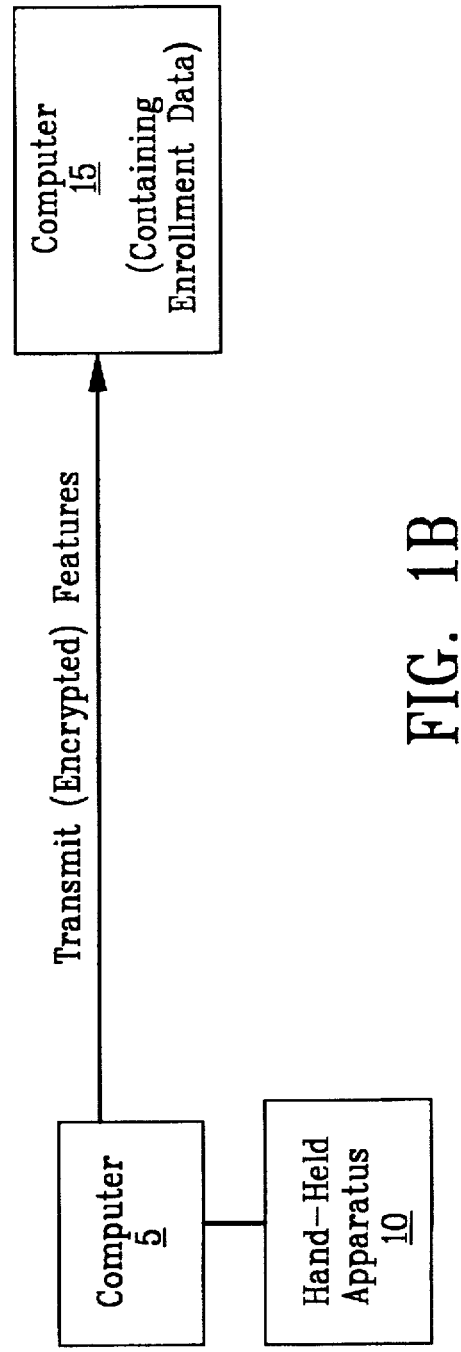
FIG. 1B is a block diagram depicting an alternate embodiment of a biometric identity verification/recognition system for remote access application in accordance with the present invention.

Referring to FIG. 1B, in another remote access embodiment, a first computer 5, configured with hand-held apparatus 10 is located at a first location. Hand-held apparatus 10 generates a source signal s(t), detects a response signal f(t), and extracts features from response signal f(t). Computer 5 then transmits (possibly encrypted) features through an output port over a transmission line; a second (commercially-available) computer 15, containing enrollment/reference data of the individual attempting access, at a second location, receives the features transmitted at an input port; the second computer 15 performs the necessary pattern recognition computations for identity verification or recognition, and remote access is allowed or disallowed. The most likely medium for signal transfer currently is an analog or digital telephone line. The data can be digitally encoded and sent via modem or telephone line.

In still another alternative embodiment, an integral system, for example, a "box" with an embedded processor is connected to the hand-held apparatus 10, that can be integrated with, for example, a card reader or PIN keypad and a door-lock mechanism in a manner that will become apparent to those of ordinary skill in the art. Specialized development can be required to implement the invention for a particular application (e.g., ATMs) in a manner that will become apparent to those of ordinary skill in the art.

In summary, the present invention provides novel systems and methods of information and asset protection. The novel biometric identity verification/recognition systems and methods presented are innovative in many respects including the following, but not limited to, through: (1) the use of an entirely new biometric—the acoustic signature of an individual's ear canal; and (2) the use of feature extraction methods which can require a different measured signal at each access attempt in order to compute the same feature vector, which reduces vulnerability to defeat. Because of these innovations, the present invention is expected to be highly reliable, convenient and comfortable to users, and capable of remote access. It has the potential to meet access control needs in many areas.

A reliable identity verification or recognition technology can have significant impact on an extremely broad range of access control and information surety applications. The present invention is expected to find use in a wide variety of cases where a person's identity is to be established. Examples include restricted facility access, intelligence information control, computer access control to accounts and information, automatic teller machines, bank account inquiries and transactions, credit card authorization, voice mail and electronic mail, identity verification for banking, credit card purchases, employee time and attendance records, facility security, airport security (e.g., authorized employees verified before entering restricted areas), fast passport verification of travelers in airports, access to restricted facilities, prisons, welfare benefits, schools (verifying parents that are authorized to remove children from school grounds), voting, etc. In each of these situations, the goal is the same—to protect controlled information or property from unauthorized access by verifying that the individual is authorized and verifying that the individual is indeed the individual whose identity the person claims.

Other variations and modifications of the present invention will become apparent to those of ordinary skill in the art, and it is the intent of the appended claims that such variations and modifications be covered. The particular values and configurations discussed above can be varied and are cited merely to illustrate a particular embodiment of the present invention and are not intended to limit the scope of the invention. It is contemplated that the use of the present invention may involve components having different characteristics as long as the principle, the presentation of a totally new biometric—the acoustic response of the ear canal, is followed. It is intended that the scope of the present invention be defined by the claims appended hereto.

The entire disclosures of all patents, patent applications, and publications cited herein are hereby incorporated by reference.

We claim:

1. A system for verifying/recognizing the identity of an individual by characterizing the acoustic properties of the ear canal as a biometric, said system comprising:

enrollment means for enrolling the individual by characterizing the acoustic properties of an ear canal of the individual; and verification means for verifying the identity of the individual by determining whether the individual has previously been enrolled during said step of enrolling the individual.

2. The system of claim 1, wherein said enrollment means comprises:
   data acquisition means for acquiring reference data from the ear canal of the individual;
   extraction means for extracting reference feature vector data; and
   storage means for storing the reference feature vector data.

3. The system of claim 2, wherein the data acquisition means comprises:
   source means for emitting a source signal s(t) as a function of time t into the ear canal of the individual; and
   detection means for detecting a response signal f(t) as a function of time in response to the source signal s(t).

4. The system of claim 3, further comprising:
   means for digitizing the response signal f(t); and
   sampling means for sampling the response signal f(t) at a high sampling rate.

5. The system of claim 4, further comprising storage means for storing the response signal f(t) once it has been digitized by said digitizing means.

6. The system of claim 2, wherein data acquisition means for acquiring data from the ear canal of the individual comprises capture means for capturing frequency and intensity information contained in the response signal f(t).

7. The system of claim 2, wherein the source signal s(t) emitted from said source means is controlled.

8. The system of claim 2, wherein the source signal s(t) emitted from said source means is broad-band noise.

9. The system of claim 1, wherein said verification means comprises:
   data acquisition means for acquiring newly-acquired data from the ear canal of the individual;
   extraction means for extracting newly-extracted feature vector data; and
   pattern recognition means for recognizing a pattern to determine if the individual has previously been enrolled.

10. The system of claim 9, wherein said pattern recognition means comprises:
    comparison means for comparing the newly-extracted feature vector data against the reference feature vector data.

11. The system of claim 9, wherein said pattern recognition means comprises a computer-implemented pattern recognition algorithm.

12. The system of claim 9, further comprising authorization means for authorizing access if the individual has been previously enrolled and for denying access if the individual has not been previously enrolled.

13. The system of claim 9, wherein the data acquisition means for acquiring newly acquired-data comprises:
    source means for emitting a source signal s(t) as a function of time t into the ear canal of the individual; and
    detection means for detecting a response signal f(t) as a function of time in response to the source signal s(t).

14. The system of claim 13, wherein the source signal s(t) is emitted in a series of pure-frequency tones until a steady state is reached in the response signal f(t) for each frequency in the series.

15. The system of claim 1, wherein said enrollment means comprises:
    a hand-held apparatus for emitting a source signal s(t) into the ear canal of the individual; and
    a computer adapted to incorporate analog-to-digital/digital-to-analog capability running a computer program that instructs the computer to acquire data from the ear canal of the individual; extract reference feature vector data; and store the reference feature vector data.

16. The system of claim 15, wherein said hand-held apparatus comprises:
    a source signal emitter for emitting a source signal s(t) into the ear canal of the individual, the ear canal responding with a response signal f(t); and
    a signal response detector for detecting the response signal f(t).

17. The system of claim 16, wherein said source signal emitter is a speaker, and wherein said signal response detector is a microphone.

18. The system of claim 16, wherein the computer digitizes and samples the response signal f(t), and wherein the response signal f(t) is stored in the computer after it is digitized.

19. The system of claim 18, wherein the response signal f(t) is analyzed via a computer-implemented method by a computer to extract feature vector data.

20. The system of claim 18, wherein the series of frequency tones is the range of zero kHz to fifty kHz.

21. The system of claim 20, wherein the range is advanced in increments of 100 Hz.

22. The system of claim 15, further comprising calibration means for calibrating the hand-held apparatus.

23. A method for verifying/recognizing the identity of an individual by characterizing the acoustic properties of the ear canal as a biometric, said method comprising the steps of:
    enrolling the individual by characterizing the acoustic properties of an ear canal of the individual a first time; and
    verifying the identity of the individual by characterizing the acoustic properties of the ear canal of the individual a second time and by determining whether the individual has previously been enrolled during said step of enrolling the individual.

24. The method of claim 23, wherein said enrolling step comprises the steps of:
    acquiring reference data from the ear canal of the individual;
    extracting reference feature vector data from the reference data; and
    storing the reference feature vector data.

25. The method of claim 24, wherein the step of acquiring reference data comprises the steps of:
    emitting source signals $s_i(t)$ as a function of time t into the ear canal of the individual; and
    detecting response signals $f_i(t)$ as a function of time in response to the step of emitting source signals $s_i(t)$.

26. The method of claim 25, further comprising the steps of:
    digitizing the response signals $f_i(t)$; and
    sampling the response signals $f_i(t)$ at a predetermined sampling rate.

27. The method of claim 26, further comprising the step of storing the response signals $f_i(t)$ after said step of digitizing the response signals $f_i(t)$.

28. The method of claim 24, wherein said step of acquiring reference data from the ear canal of the individual comprises the step of capturing frequency and intensity information contained in response signals f(t), the response signals f(t) being generated in response to the source signals s(t) emitted in the ear canal of the individual.

29. The method of claim 23, wherein said verifying step comprises the steps of:

acquiring newly-acquired data from the ear canal of the individual;

extracting newly-extracted feature vector data from the newly-acquired data; and recognizing a pattern in the newly-extracted feature vector data to determine if the individual has previously been enrolled.

30. The method of claim 29, wherein said step of recognizing a pattern comprises the step of comparing the newly-extracted feature vector data against the reference feature vector data obtained during said step of enrolling an individual.

31. The method of claim 29, wherein said step of recognizing a pattern is performed using a computer-implemented pattern recognition algorithm.

32. The method of claim 29, further comprising the step of authorizing access if the individual has been previously enrolled.

33. The method of claim 29, further comprising the step of denying access if the individual has not been previously enrolled.

34. The method of claim 29, wherein the step of acquiring newly-acquired data comprises the steps of:

emitting source signals $s_2(t)$ as a function of time t into the ear canal of the individual; and detecting response signals $f_2(t)$ as a function of time in response to the step of emitting source signals $s_2(t)$.

35. The method of claim 23, wherein said step of enrolling an individual uses reference feature vector data to characterize the individual, and wherein said step of verifying the identity of the individual uses newly-acquired feature vector to characterize the individual.

36. The method of claim 35, wherein the reference feature vector data and the newly-acquired feature vector data are extracted from response signals f(t), the response signals f(t) being generated in response to source signals s(t) emitted in the ear canal of the individual, the response signals f(t) being described as a convolution of the source signals s(t) with an effective impulse response function of the ear canal h(t).

37. The method of claim 35, wherein the reference feature vector data and the newly-acquired feature vector data are extracted from a discrete Fast Fourier Transform F($\omega$) of response signals f(t), where $\omega$ is natural frequency and t is time, the response signals f(t) being generated in response to the source signals s(t) emitted in the ear canal of the individual.

38. The method of claim 35, wherein the reference feature vector data and the newly-acquired feature vector data are directly extracted from source signals s(t) emitted in the ear canal of the individual.

39. The method of claim 35, wherein the reference feature vector data and the newly-acquired feature vector data are described as a discretized log $|H(\omega)|^2$, where is the natural frequency and H($\omega$) is the Fourier transform of an effective impulse response function of the ear canal h(t).

40. The method of claim 35, wherein the reference feature vector data and the newly-acquired feature vector data are described by a discretized function H($\omega$) as a function of natural frequency $\omega$, where $\omega$ is the natural frequency and H($\omega$) is the Fourier transform of an effective impulse response function of the ear canal h(t).

41. The method of claim 35, wherein the reference feature vector data and the newly-acquired feature vector data are described by a discretized function h(t) as a function of time t, where h(t) is an effective impulse response function of the ear canal.

42. A system for biometric identification, said system comprising means for determining the identification of an individual by analyzing the acoustic properties of an ear canal of the individual, said means comprising a computer adapted to incorporate analog-to-digital and digital-to-analog capability running a computer program that instructs the computer to acquire data from the ear canal of the individual; extract reference features; store the reference features in a storage medium, and read the reference features from the storage medium to determine the identity of the individual.

43. A method for biometric identification, said method comprising the steps of:

enrolling an individual to obtain reference data;

transmitting signals s(t) into an ear canal of the individual;

detecting response signals f(t) from the ear canal of the individual in response to the transmitting signals step; and comparing the response signals f(t) with the previously obtained signals emitted from the ear canal of the individual to verify the identity of the individual.

44. The method of claim 43, wherein said enrolling step comprises the steps of:

acquiring data;

extracting feature data; and storing the feature data.

45. The method of claim 43, wherein said comparing step comprises the step of reading the reference data from a storage means.

46. The method of claim 43, wherein the response signals represent acoustic properties of the ear canal of the individual.

47. A system for biometric identification, said system comprising:

acquisition means for storing biometric information from an ear canal of an individual;

source means for transmitting source signals into an ear canal of the individual;

recording means for recording response signals emitted from the ear canal of the individual; and verification means for verifying that the response signals match the biometric information from the ear canal of the individual to verify the identity of the individual.

48. The system of claim 47, wherein said verification means comprises a pattern recognition algorithm.

49. The system of claim 47, wherein said pattern recognition algorithm is computer implemented.

50. A method for verifying/recognizing the identity of an individual by characterizing the acoustic properties of the ear canal as a biometric, said method comprising the steps of:

enrolling the individual by characterizing the acoustic properties of an ear canal of the individual, wherein said enrolling step comprises the steps of:

acquiring reference data from the ear canal of the individual by emitting source signals $s_1(t)$ as a function of time t into the ear canal of the individual and detecting response signals $f_1(t)$ as a function of time that are generated in response to the source signals s(t);

extracting reference feature vector data from the reference data; and storing the reference feature vector data; and verifying the identity of the individual by determining whether the individual has previously been enrolled during said step of enrolling the individual, wherein said verifying step comprises the steps of:

acquiring newly-acquired data from the ear canal of the individual by emitting source signals $s_2(t)$ as a function of time t into the ear canal of the individual and detecting response signals $f_2(t)$ as a function of time that are generated in response to the source signals $s_2(t)$;

extracting newly-extracted feature vector data from the newly-acquired data; and recognizing a pattern in the newly-extracted feature vector data to determine if the individual has previously been enrolled.

51. The method of claim 50, wherein said step of recognizing a pattern comprises the step of comparing the reference feature vector data against the newly-acquired feature vector data.

52. A system for characterizing an individual by characterizing the acoustic properties of the ear canal as a biometric, said system comprising:

transmitting means for transmitting a first signal into the ear canal of the individual;

receiving means for receiving a second signal characteristic of an individual in response to the first signal; and means for characterizing the individual by characterizing the acoustic properties of the ear canal as a biometric based on the second signal.

53. The system of claim 52, wherein said transmitting means and said receiving means is a transceiver.

54. The system of claim 52, wherein said transmitting means is a speaker and wherein said receiving means is a microphone.

55. A system for remote access biometric identification, said system comprising:

enrollment means, located at a first location, for enrolling the individual by characterizing the acoustic properties of an ear canal of the individual and for generating and transmitting source signals s(t) into an ear canal of an individual;

receiving means, located at a second location, for receiving said source signals s(t) and for detecting and transmitting response signals f(t) to the first location, the response signals f('t) being generated in response to source signals s(t); and verifying means, located at the first location, for receiving response signals f(t) and for verifying the identity of the individual.

56. The system of claim 55, wherein:

said enrollments means is a computer adapted to incorporate analog-to-digital/digital-to-analog capability and running a computer program that instructs the computer to acquire data from the ear canal of the individual; extract reference feature vector data; and store the reference feature vector data;

said receiving means is a transceiver; and said verifying means is the computer.

57. A system for remote access biometric identification, said system comprising:

source means, located at a first location, for emitting source signals s(t) into an ear canal of an individual, the ear canal generating response signals f(t) in response to source signals s(t);

detecting means, located at the first location, for detecting the response signals f(t);

extracting means, located at the first location, for extracting features from the response signals f(t);

transmitting means, located at the first location, for transmitting the features to a second location; and comparing means, located at the second location, for receiving the features and for comparing the features against reference features that characterize the individual.

* * * * *